US007771321B2

(12) United States Patent
Hirata et al.

(10) Patent No.: US 7,771,321 B2
(45) Date of Patent: Aug. 10, 2010

(54) EXERCISE MANAGEMENT SYSTEM

(75) Inventors: Takashi Hirata, Wako (JP); Ken Yasuhara, Wako (JP); Kei Shimada, Wako (JP)

(73) Assignee: Honda Motor Co., Ltd., Tokyo (JP)

(*) Notice: Subject to any disclaimer, the term of this patent is extended or adjusted under 35 U.S.C. 154(b) by 13 days.

(21) Appl. No.: 12/295,759

(22) PCT Filed: Mar. 26, 2007

(86) PCT No.: PCT/JP2007/056194

§ 371 (c)(1),
(2), (4) Date: Oct. 2, 2008

(87) PCT Pub. No.: WO2007/116681

PCT Pub. Date: Oct. 18, 2007

(65) Prior Publication Data

US 2009/0137366 A1 May 28, 2009

(30) Foreign Application Priority Data

Apr. 6, 2006 (JP) ............................. 2006-105182

(51) Int. Cl.
*A63B 71/00* (2006.01)
(52) U.S. Cl. .................. 482/9; 482/8; 482/54; 482/901
(58) Field of Classification Search .................. 482/1–9, 482/51, 54, 900–902; 434/247; 119/700
See application file for complete search history.

(56) References Cited

U.S. PATENT DOCUMENTS 5,961,541 A * 10/1999 Ferrati ......................... 607/49

6,605,020 B1 * 8/2003 Huang .......................... 482/54
7,065,408 B2 * 6/2006 Herman et al. ................ 607/49

FOREIGN PATENT DOCUMENTS

| EP | 0 782 843 | 7/1997 |
|---|---|---|
| EP | 1 547 567 | 6/2006 |

(Continued)

*Primary Examiner*—Glenn Richman
(74) *Attorney, Agent, or Firm*—Rankin, Hill & Clark LLP

(57) ABSTRACT

A system for managing exercise of an animal such as a human being so that the motion of the animal is induced with an appropriate scale and rhythm in accordance with the physiological conditions of the animal is provided. According to the exercise management system (1) of the present invention, during the process where the user's walking motion is induced by an operation of a walking motion induction device (20), a walking ratio (k) and a physiological variable such as consumed energy are measured. Then, the walking ratio (k) in the state where the physiological variable attains an appropriate value in consideration of activation of physical functions or reduction of body load of the user is set as a recommended walking ratio ($k_0$). This ensures that the recommended walking ratio ($k_0$) is set as appropriate in consideration of activation of the physical functions of the user or the like. As the walking motion is induced based on this recommended walking ratio ($k_0$) by the walking motion induction device (20), the induction scale and rhythm can be controlled appropriately so that the step width (q) and the walking rate (p) are appropriate in consideration of activation of the physical functions of the user or the like.

6 Claims, 8 Drawing Sheets

FOREIGN PATENT DOCUMENTS

| | | |
|---|---|---|
| JP | H05-35160 | 5/1993 |
| JP | 10-043327 | 2/1998 |
| JP | 10-099390 | 4/1998 |
| JP | 2001-238982 | 9/2001 |
| JP | 2001-346906 | 12/2001 |
| JP | 2003-154029 | 5/2003 |
| JP | 2004-073649 | 3/2004 |
| WO | 00/28927 | 5/2000 |
| WO | 02/15819 | 2/2002 |

* cited by examiner

EXERCISE MANAGEMENT SYSTEM

TECHNICAL FIELD

The present invention relates to a system and method for managing exercise of an animal, and a program for providing a computer with the management function.

BACKGROUND ART

There has been proposed a technique to determine an appropriate walking speed in consideration of a physiological index such as a user's electrocardiographic signal, for the purposes of setting a level of walking training for the user (for example, see Japanese Patent Application Laid-Open No. 2003-154029).

DISCLOSURE OF THE INVENTION

Problem to be Solved by the Invention

In the case where a device for inducing (or assisting) motion of the user's legs and the like by applying a force to the user's body is attached to the user, however, it has not been considered to set an induction scale and rhythm suitable for that user.

In view of the foregoing, it is an object of the present invention to provide a system and method for managing exercise of an animal such as a human being so that its motion can be induced with an appropriate scale and rhythm in accordance with its physiological conditions, and a program for providing a computer with that management function.

Means for Solving the Problem

An exercise management system according to a first invention to achieve the above object includes: a control unit which controls an operation of a second motion induction device inducing motion of the animal while adjusting a motion scale of the animal at a rhythm harmonized with a motion rhythm of the animal; a physiological variable measuring unit which measures a physiological variable representing a physiological condition of the animal; a motion variable measuring unit which measures a motion variable representing one or both of the motion scale and the motion rhythm of the animal; and a recommended value setting unit which sets, as a recommended value of the motion variable, the motion variable that is measured by the motion variable measuring unit at the time when the physiological variable measured by the physiological variable measuring unit in the state where the motion of the animal is induced by the operation of the second motion induction device that is controlled by the control unit to change the motion variable attains an appropriate value in consideration of activation of physical functions or reduction of body load of the animal.

According to the exercise management system of the first invention, the physiological variable and motion variable of the animal are measured in the state where the motion of the animal is induced by the operation of the second motion induction device. The "physiological variable" represents the physiological condition of the animal. The "motion variable" represents one or both of the motion scale and motion rhythm of the animal. The value of the motion variable obtained at the time when the physiological variable attains an appropriate value in consideration of "activation of physical functions" or "reduction of body load" of the animal is set as the recommended value of the motion variable. This ensures that the recommended value of the motion variable of the animal is set as appropriate in consideration of activation of the physical functions of the animal or the like. The motion of the animal is then induced by the second motion induction device according to this recommended value, which allows the induction scale and the induction rhythm to be controlled appropriately so that the motion scale and the motion rhythm of the animal are appropriate in consideration of activation of the physical functions of the animal or the like. In other words, the motion of the animal can be induced with an appropriate scale and rhythm in consideration of activation of the physical functions or the like, in accordance with the physiological conditions of the animal.

Further, an exercise management system according to a second invention is characterized in that, in the exercise management system of the first invention, the control unit includes: a motion oscillator measuring unit which measures first and second motion oscillators as parameters that periodically change in accordance with the motion of the animal; a first oscillator generating unit which inputs the first motion oscillator measured by the motion oscillator measuring means as an input oscillation signal to a first model which generates an output oscillation signal that changes over time at an angular velocity determined based on a natural angular velocity by mutual entrainment with the input oscillation signal, to generate a first oscillator as the output oscillation signal; a natural angular velocity setting unit which sets a new natural angular velocity based on a phase difference between the motion oscillator measured by the motion oscillator measuring unit and the first oscillator generated by the first oscillator generating unit; a second oscillator generating unit which inputs the second motion oscillator measured by the motion oscillator measuring means as an input oscillation signal to a second model which generates an output oscillation signal that changes over time at an angular velocity determined based on the natural angular velocity set by the natural angular velocity setting means, to generate a second oscillator as the output oscillation signal; and an induction oscillator generating unit which generates an induction oscillator specifying a scale and rhythm of the operation of the second motion induction device, based on the motion variable measured by the motion variable measuring unit in addition to the second oscillator generated by the second oscillator generating unit.

According to the exercise management system of the second invention, mutual adaptation or harmonization is established between the motion rhythm of the animal and the operation rhythm (inducing the motion of the animal) of the second motion induction device. This allows the motion of the animal to be induced at an appropriate scale and rhythm in consideration of activation of the physical functions or the like, while harmonizing the motion of the animal with the operation of the second motion induction device.

Further, an exercise management system according to a third invention is characterized in that, in the exercise management system of the first invention, the physiological variable measuring unit measures part or all of oxygen uptake, respiratory frequency, heart rate, pulse rate, blood pressure, arterial oxygen saturation, lactate level, myogenic potential, and consumed energy of the animal as the physiological variable.

According to the exercise management system of the third invention, the motion of the animal can be induced at an appropriate scale and rhythm in consideration of activation of the physical functions or the like, in accordance with the physiological condition represented by the oxygen uptake of the animal or the like.

Further, an exercise management system according to a fourth invention is characterized in that, in the exercise management system of the first invention, the motion variable measuring unit includes a first motion variable measuring unit and a second motion variable measuring unit, the first motion variable measuring unit measures a first motion variable based on an operation speed of a first motion induction device which induces the motion of the animal while adjusting a motion speed of the animal, the first motion variable being the motion variable representing the motion scale and the motion rhythm of the animal the motion of which is induced by an operation of the first motion induction device, and the second motion variable measuring unit measures a second motion variable based on either a state of interaction between the first motion induction device and the animal or an operating state of the second motion induction device, the second motion variable being the motion variable representing the motion rhythm or the motion scale of the animal.

According to the exercise management system of the fourth invention, the "first motion variable" is measured based on the speed of operation of the first motion induction device. Further, the "second motion variable" is measured based on either the interaction between the first motion induction device and the animal or the induction scale or induction rhythm by the second motion induction device. This improves the measurement accuracies of the first and second motion variables and of the motion variable as their function. Accordingly, it is possible to set a more appropriate recommended value of the motion variable in consideration of activation of the physical functions of the animal or the like.

Further, an exercise management system according to a fifth invention is characterized in that, in the exercise management system of the fourth invention, the first motion variable measuring unit measures a walking or running speed of the animal as the first motion variable, and the second motion variable measuring unit measures a step width of the animal or a walking rate corresponding to the number of steps per unit time of the animal as the second motion variable.

According to the exercise management system of the fifth invention, the recommended value of the motion variable, which is a function of walking or running speed of the animal and step width or walking rate, may be set as appropriate in consideration of activation of the physical functions and/or reduction of body load of the animal. The walking or running speed represents the motion scale and the motion rhythm of the animal. The step width represents the motion scale of the animal. The walking rate represents the motion rhythm of the animal. As the motion of the animal is induced based on this recommended value by the second motion induction device, the induction scale and rhythm may be controlled appropriately so that the step width or walking rate of the animal becomes appropriate in consideration of activation of the physical functions of the animal or the like.

Further, an exercise management system according to a sixth invention is characterized in that, in the exercise management system of the fifth invention, the motion variable measuring unit measures, as the motion variable, a walking ratio corresponding to either a ratio of a square of the step width as the second motion variable with respect to the walking or running speed as the first motion variable, or a ratio of the walking or running speed as the first motion variable with respect to a square of the walking rate as the second motion variable.

According to the exercise management system of the sixth invention, the recommended value of the walking ratio of the animal may be set as appropriate in consideration of activation of the physical functions and/or reduction of body load of the animal. Then, with the motion of the animal induced by the second motion induction device based on this recommended value, the induction scale and rhythm may be controlled appropriately so that the walking ratio of the animal becomes appropriate in consideration of activation of the physical functions of the animal or the like.

Further, an exercise management system according to a seventh invention is characterized in that, in the exercise management system of the fourth invention, the first motion variable measuring unit measures the first motion variable of the animal the motion of which is being induced in a direction opposite from the direction of circular movement of a circular motion body provided in the first motion induction device, based on a speed of the circular movement of the circular motion body.

According to the exercise management system of the seventh invention, the circular motion body provided in the first motion induction device is caused to perform circular movement to induce the motion of the animal whose body part is in contact with the circular motion body in the direction opposite from the direction of the circular movement of the circular motion body. The "circular motion body" may be: an endless belt looped over a plurality of rollers; a spherical body or oval sphere circulated about an axis passing the center or a point offset from the center; a tubular body such as a cylinder or square pole circulated about a central axis or an axis offset from and parallel to the central axis; or a block of substance circulated about an arbitrary axis. As the movement of the animal or its body part in accordance with its motion is cancelled out by the circular movement of the circular motion body, the recommended value of the motion variable of the animal can be set only if there is a space for installing the first motion induction device, and the space for installation can be selected relatively freely.

Further, an exercise management system according to an eighth invention is characterized in that, in the exercise management system of the fourth invention, the first motion variable measuring unit measures the walking or running speed as the first motion variable representing a speed of the walking or running motion of the animal which is induced in a direction opposite from the movement of an endless belt serving as a circular motion body that is looped over a plurality of rollers provided in a treadmill serving as the first motion induction device, based on a driven speed of the endless belt.

According to the exercise management system of the eighth invention, the circular movement of the endless belt (circular motion body) of the treadmill (first motion induction device) induces the walking or running motion of the animal in the direction opposite from the direction of the circular movement of the endless belt. As the movement of the animal by the walking or running motion is cancelled out by the circular movement of the endless belt, the recommended value of the motion variable for the walking or running motion of the animal can be set only if there is a space for installing the first motion induction device, and the installation space can be selected relatively freely.

Further, an exercise management system according to a ninth invention is characterized in that, in the exercise management system of the first invention, the recommended value setting unit preliminarily sets a plurality of recommended values for a plurality of animals, respectively, by recognizing identifiers for identification of physical characteristics of the respective animals, and newly sets the recommended value based on the recommended value preliminarily set for each identifier recognized, to establish a database having the identifiers and the recommended values associated with each other.

According to the exercise management system of the ninth invention, typical recommended values are set in accordance with the physical characteristics of the respective animals (including the body size, weight, age, gender and the like). With the motion of the animal induced based on this typical recommended value by the second motion induction device, the induction scale and rhythm may be controlled appropriately so that the motion variable of the animal becomes appropriate in consideration of activation of the physical functions of the animal or the like.

A method according to a tenth invention to achieve the above object is a method for managing exercise of an animal, which includes the steps of: controlling an operation of a second motion induction device inducing motion of the animal while adjusting a motion scale of the animal at a rhythm harmonized with a motion rhythm of the animal; measuring a physiological variable representing a physiological condition of the animal; measuring a motion variable representing one or both of the motion scale and the motion rhythm of the animal; and setting, as a recommended value of the motion variable, the motion variable measured at the time when the physiological variable measured while the motion of the animal is induced by the operation of the second motion induction device controlled by the control unit to change the motion variable attains an appropriate value in consideration of activation of physical functions or reduction of body load of the animal.

According to the exercise management method of the tenth invention, as in the exercise management system of the first invention, the recommended value of the motion variable of the animal may be set as appropriate in consideration of activation of the physical functions of the animal or the like. The motion of the animal is then induced by the second motion induction device according to this recommended value, which allows the induction scale and the induction rhythm to be controlled appropriately so that the motion scale and the motion rhythm of the animal become appropriate in consideration of activation of the physical functions of the animal or the like.

A program according to an eleventh invention to achieve the above object is a program for causing a computer to function as a system for managing exercise of an animal, which is characterized by causing the computer to function as the system including: a control unit which controls an operation of a second motion induction device inducing motion of the animal while adjusting a motion scale of the animal at a rhythm harmonized with a motion rhythm of the animal; a physiological variable measuring unit which measures a physiological variable representing a physiological condition of the animal; a motion variable measuring unit which measures a motion variable representing one or both of the motion scale and the motion rhythm of the animal; and a recommended value setting unit which sets, as a recommended value of the motion variable, the motion variable that is measured by the motion variable measuring unit at the time when the physiological variable measured by the physiological variable measuring unit in the state where the motion of the animal is induced by the operation of the second motion induction device controlled by the control unit to change the motion variable attains an appropriate value in consideration of activation of physical functions or reduction of body load of the animal.

According to the exercise management program of the eleventh invention, the computer is provided with the functions of managing exercise of the animal in such a manner that the recommended value of the motion variable of the animal may be set as appropriate in consideration of activation of the physical functions of the animal or the like. The functions may be provided to a single computer, or to a plurality of computers in a distributed manner.

BEST MODE FOR CARRYING OUT THE INVENTION

Embodiments of the exercise management system, exercise management method, and exercise management program of the present invention will be described with reference to the drawings. Hereinafter, subscripts L and R will be attached to parameters to make a distinction between left and right for walker's legs or the like, although the subscripts L and R are omitted in the case where such distinction is not particularly necessary, for simplicity of notation.

The configuration of the exercise management system of the present invention will now be described with reference to FIG. 1.

Figure 1:
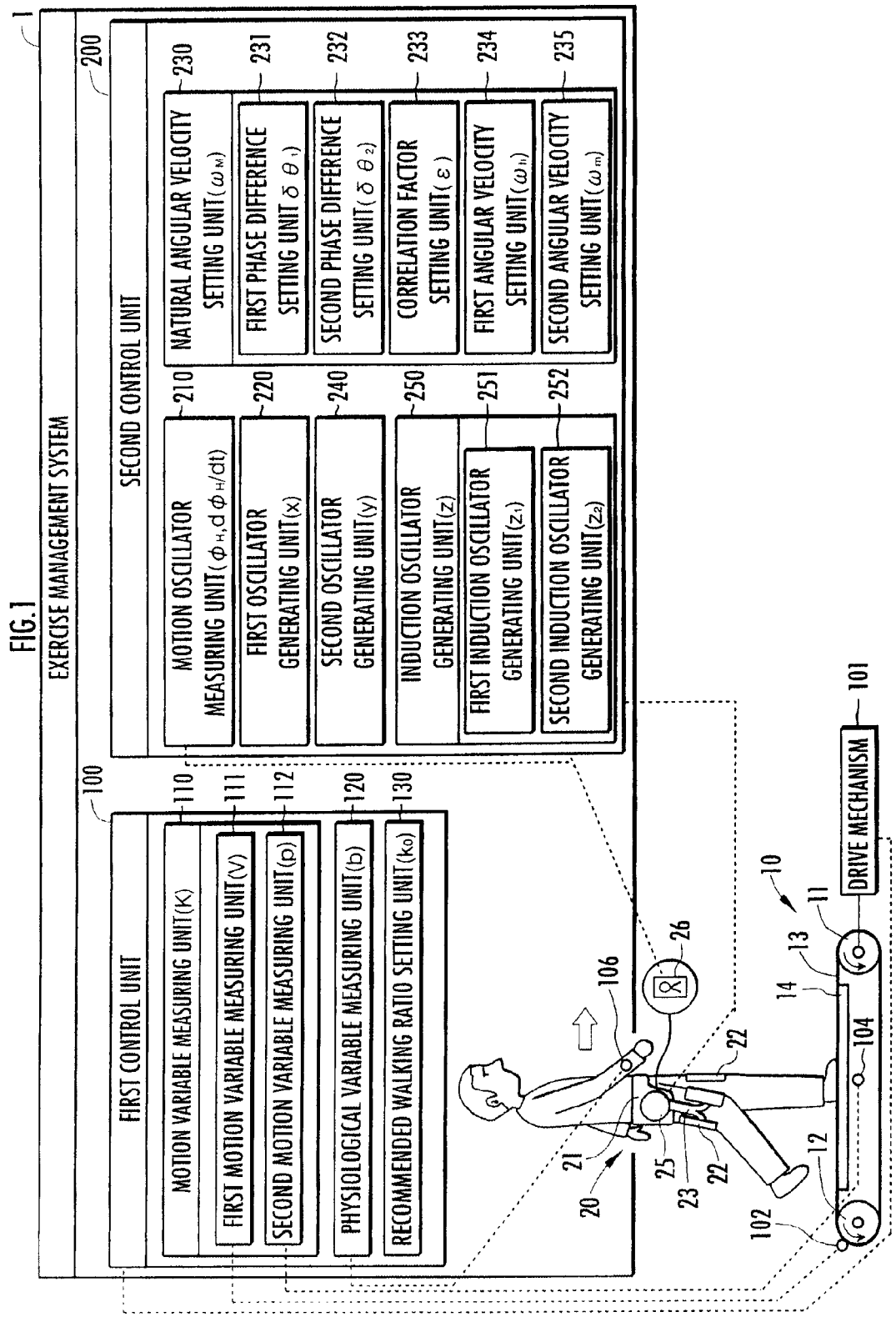
FIG. 1 is an illustrative configuration diagram of an exercise management system of the present invention.

An exercise management system 1 shown in FIG. 1 includes a treadmill (first motion induction device) 10 and a walking motion induction device (second motion induction device) 20. The exercise management system 1 is for setting a recommended walking ratio suitable in consideration of activation of physical functions of a user (human being (animal)) or the like, using the treadmill (first motion induction device) 10 and the walking motion induction device (second motion induction device) 20. The exercise management system 1 is also for training the user by causing the user to walk with a scale and rhythm corresponding to the recommended walking ratio, while realizing harmonization between the user's walking or running motion, the operation of the treadmill 10, and the operation of the walking motion induction device 20.

The treadmill 10 includes a driving roller 11 having a width slightly wider than the typical width of the human being, a driven roller 12 having an approximately same width as the driving roller 11, an endless belt (rotating body) 13 looped over the driving roller 11 and the driven roller 12, and a footplate 14 which supports from below the portion of the endless belt 13 on which the user stands. The driving roller 11 is driven by a drive mechanism 101 composed of a motor, transmission and the like. As the driving roller 11 is driven in the clockwise direction in the figure, the belt 13 rotates in the clockwise direction with the driven roller 12 driven in the same direction. This induces the user on the belt 13 to walk (or run) to the right in the figure. Further provided are a speed sensor 102 which outputs a signal responsive to the moving speed of the belt 13, and a pressure sensor 104 which outputs a signal responsive to the pressure received by the footplate 14. A physiological variable sensor 106, which is attached to the user's body, outputs a signal responsive to a physiological variable b such as the heart rate. The physiological variable sensor 106 is attached to the user's body in a suitable manner depending on the physiological variable b to be used. The treadmill 10 may be of any known configuration, including a commercially available one.

The walking motion induction device 20 includes a waist orthosis 21, thigh orthoses 22, force transmitting members 23, a battery 24, actuators (electric motors) 25, and hip joint angle sensors 26.

The waist orthosis 21 is made of rigid and flexible materials combined, and is attached to a user's waist. The thigh orthosis 22 is also made of combined rigid and flexible materials, and is attached to each of the front and back of a user's thigh. The force transmitting member 23, which is made of lightweight rigid plastic or any other material having a good shape retention property, extends downward from each side of the user's waist along the user's corresponding thigh and then bifurcates toward the front and back of the thigh. It is connected to the actuator 25 and the respective thigh orthoses 22. The battery 24 is housed in the waist orthosis 21 (for example, fixed between a plurality of materials constituting the waist orthosis 21) and supplies electric power to the actuator 25 and the like. The actuator 25 is mounted on the waist orthosis 21 and applies a force to the user's thigh via the force transmitting member 23 and the thigh orthosis 22. The hip joint angle sensor 26 is composed of a rotary encoder and the like provided on each of the sides of the user's waist, and outputs a signal responsive to a hip joint angle.

The exercise management system 1 includes a first control unit 100 and a second control unit 200.

The first control unit 100 is composed of a computer such as a microcomputer attached to the treadmill 10, and controls the speed of the driving roller 11 driven by the drive mechanism 102 and the like. The first control unit 100 includes a motion variable measuring unit 110, a physiological variable measuring unit 120, and a recommended walking ratio setting unit 130. The motion variable measuring unit 110, the physiological variable measuring unit 120, and the recommended walking ratio setting unit 130 are each composed of a computer (containing CPU, ROM, RAM, I/O (input/output device) and others) serving as hardware and a part of the "exercise management program" of the present invention serving as software for providing functions to the computer.

The motion variable measuring unit 110 includes a first motion variable measuring unit 111 and a second motion variable measuring unit 112. The motion variable measuring unit 110 measures a walking ratio k ($=v/p^2$) as a motion variable, which is a function of walking speed v and walking rate p.

The first motion variable measuring unit 111 measures the user's walking speed v as a first motion variable, based on an output of the speed sensor 102. The walking speed v increases as the user's walking motion scale increases or the walking motion rhythm becomes faster, and thus, the first motion variable corresponds to the motion variable representing both the motion scale and the motion rhythm of the user.

The second motion variable measuring unit 112 measures the user's walking rate (the number of steps per unit time) p as a second motion variable, based on an output of the pressure sensor 104. The walking rate p increases as the user's walking rhythm becomes faster, and thus, the second motion variable corresponds to the motion variable representing the motion rhythm of the user.

The physiological variable measuring unit 120 measures a physiological variable b representing the user's physiological condition, based on an output of the physiological variable sensor 106 attached to the user's body.

The recommended walking ratio setting unit 130 sets a recommended walking ratio $k_0$, based on the user's walking ratio k measured by the motion variable measuring unit 110 and the physiological variable b measured by the physiological variable measuring unit 120.

The second control unit (corresponding to the "control unit" of the present invention) 200 is composed of a computer housed in the waist orthosis 21 of the walking motion induction device 20 and the "exercise management program" of the present invention serving as the software providing the computer with the control function of the walking motion induction device 20 and the like.

The second control unit 200 includes a motion oscillator measuring unit 210, a first oscillator generating unit 220, a natural angular velocity setting unit 230, a second oscillator generating unit 240, and an induction oscillator generating unit 250.

The motion oscillator measuring unit 210 measures the user's hip joint angle $\phi_H$, based on an output of the hip joint angle sensor 26, as a "second motion oscillator" that periodically changes according to the walking motion. The hip joint angle $\phi_H$ increases in amplitude as the user's walking motion scale (represented by the step width or the like) increases, and thus, it corresponds to the motion oscillator representing the user's motion scale. Further, the motion oscillator measuring unit 210 measures a hip joint angular velocity $d\phi_H/dt$ as a "first motion oscillator", based on an output of the hip joint angle sensor 26. The hip joint angular velocity $d\phi_H/dt$ increases in amplitude as the user's walking motion rhythm (represented by the waking rate or the like) becomes faster, and thus, it corresponds to the motion oscillator representing the user's motion rhythm.

The first oscillator generating unit 220 generates a first oscillator x according to a first model, based on the hip joint angular velocity $d\phi_H/dt$ measured by the motion oscillator measuring unit 210 and a natural angular velocity $\omega_M$. The "first model" is a model for generating an output oscillation signal that changes over time at an angular velocity determined based on the natural angular velocity $\omega_M$, by mutual entrainment with the input oscillation signal.

The natural angular velocity setting unit 230 includes a first phase difference setting unit 231, a second phase difference setting unit 232, a correlation factor setting unit 233, a first angular velocity setting unit 234, and a second angular velocity setting unit 235.

The first phase difference setting unit 231 sets a phase difference between the angular velocity $\omega_H$ of the hip joint angular velocity $d\phi_H/dt$ and the oscillator x reflecting the natural angular velocity $\omega_M$ included in a van der Pol equation, as a first phase difference $\delta\theta_1$.

The second phase difference setting unit 232 sets, based on a "virtual model" representing the relationship between a virtual motion oscillator $\theta_h$ and a virtual induction oscillator $\theta_m$, a phase difference between the virtual motion oscillator $\theta_h$ and the virtual induction oscillator $\theta_m$ as a second phase difference $\delta\theta_2$ ($=\theta_h-\theta_m$).

The correlation factor setting unit 233 sets a correlation factor $\epsilon$ between the virtual motion oscillator $\theta_h$ and the virtual induction oscillator $\theta_m$ so that the second phase difference $\delta\theta_2$ set by the second phase difference setting unit 232 approaches the first phase difference $\delta\theta_1$ set by the first phase difference setting unit 231.

The first angular velocity setting unit 234 sets an angular velocity $\omega_h$ of the virtual motion oscillator $\theta_h$, based on the correlation factor $\epsilon$ set by the correlation factor setting unit 233.

The second angular velocity setting unit 235 sets an angular velocity $\omega_m$ of the virtual induction oscillator $\theta_m$, as a new natural angular velocity $\omega_M$, based on the angular velocity $\omega_h$ of the virtual motion oscillator $\theta_h$ set by the first angular velocity setting unit 234, so that the second phase difference $\delta\theta_2$ set by the second phase difference setting unit 232 approaches a target phase difference $\delta\theta_d$ set by a target phase difference setting unit 212.

The second oscillator generating unit 240 generates a second oscillator y, according to a second model, based on the hip joint angle $\phi_H$ measured by the motion oscillator measuring unit 210 and the natural angular velocity $\omega_M$ set by the natural angular velocity setting unit 230. The "second model" is a model for generating an output oscillation signal that changes over time at the angular velocity determined based on the natural angular velocity $\omega_M$, based on an input oscillation signal.

The induction oscillator generating unit 250 includes a first induction oscillator generating unit 251 and a second induction oscillator generating unit 252.

The first induction oscillator generating unit 251 generates a first induction oscillator $z_1$ based on the second oscillator y generated by the second oscillator generating unit 240 and the natural angular velocity $\omega_M$ set by the natural angular velocity setting unit 230. The first induction oscillator $z_1$ represents an elastic force of an elastic element, such as a virtual spring, that causes the hip joint angle $\phi_H$ measured by the motion oscillator measuring unit 210 to approach its target value $\phi_0$. The second induction oscillator generating unit 252 generates a second induction oscillator $z_2$ based on the second oscillator y generated by the second oscillator generating unit 240 and the natural angular velocity $\omega_M$ set by the natural angular velocity setting unit 230. It represents a damping force of a damping element, such as a virtual damper, that suppresses an increase in absolute value of the hip joint angle $\phi_H$ according to the hip joint angular velocity $d\phi_H/dt$ measured by the motion oscillator measuring unit 210. Then, the induction oscillator generating unit 250 generates an induction oscillator z, based on the first induction oscillator $z_1$ and the second induction oscillator $z_2$, as an instruction signal of the torque T around the hip joint which is to be applied to the user by the walking motion induction device 20.

The first control unit 100 and the second control unit 200 are communicable in a wireless manner. It is noted that the plurality of processing units 110 (111, 112), 120, 130, 210, 220, ... constituting the exercise management system may be arranged in any arbitrary pattern in the first control unit 100 and the second control unit 200; for example, the recommended walking ratio setting unit 130 may be provided in the second control unit 200 instead of the first control unit 100. Further, the first control unit 100 and the second control unit 200 may be configured with a same computer. The first control unit 100 and the second control unit 200 may also communicate with each other via a cable.

The functions of the exercise management system 1 having the above-described configuration, particularly the method for setting the recommended walking ratio (recommended value of the motion variable) for the user, will now be described with reference to FIGS. 2 to 5.

The first control unit 100 controls the operation of the treadmill 10 to keep the speed of the belt 13 constant, to thereby induce the user's walking motion in the opposite direction from the movement of the belt 13 at an approximately constant speed.

Figure 2:
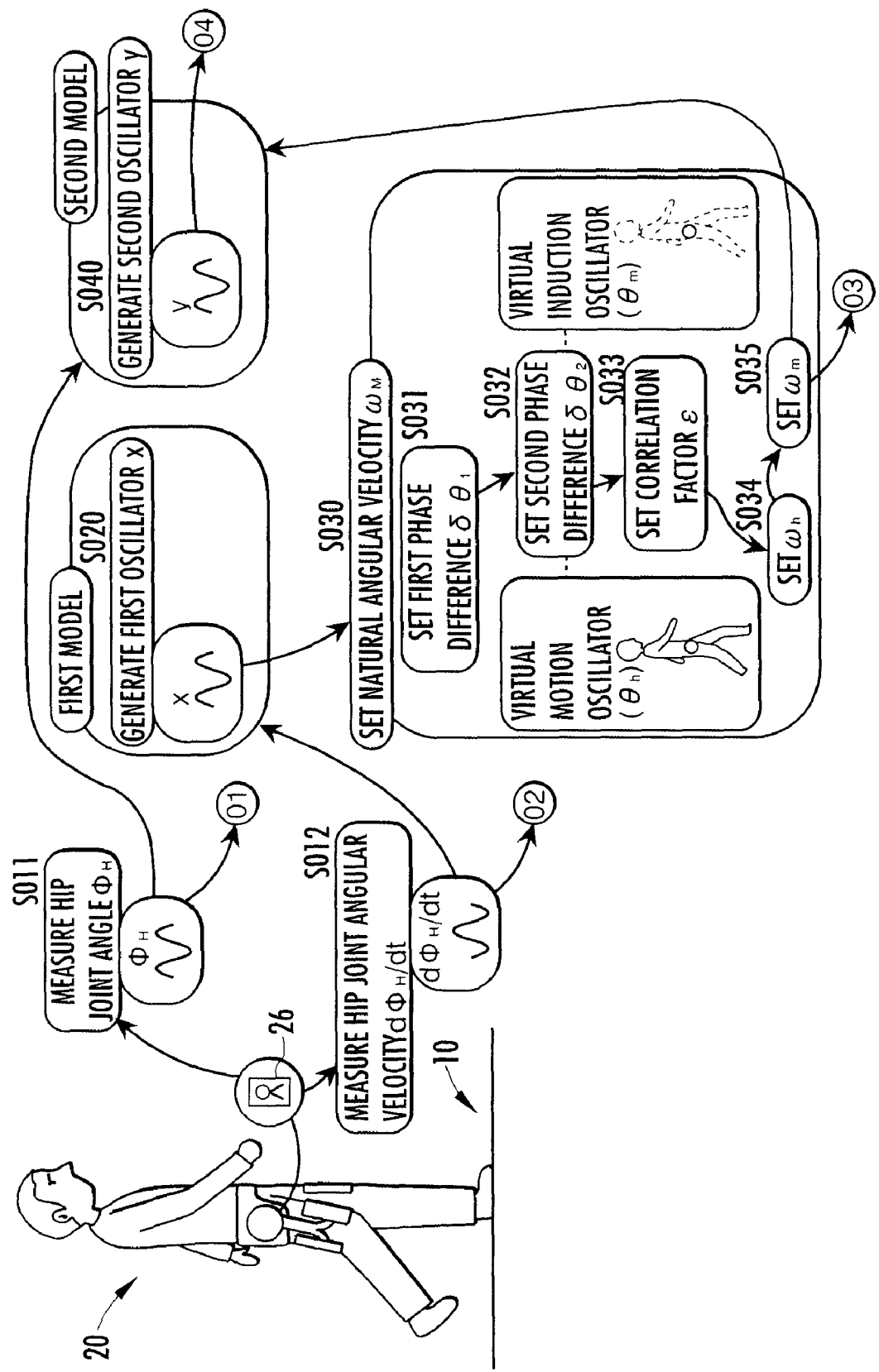
FIG. 2 is an explanatory diagram regarding an exercise management method of the present invention.

In this state, the motion oscillator measuring unit 210 measures the user's left and right hip joint angles $\phi_H=(\phi_{FL}, \phi_{HR})$, based on the outputs of the hip joint angle sensors 26 (s011 in FIG. 2). Further, the motion oscillator measuring unit 210 measures the user's left and right hip joint angular velocities $d\phi_H/dt=(d\phi_{HL}/dt, d\phi_{HR}/(dt)$, based on the outputs of the hip joint angle sensors 26 (s012 in FIG. 2).

The first oscillator generating unit 220 generates a first oscillator $x=(x_L, x_R)$ according to the "first model", based on the hip joint angular velocity $d\phi_H/dt$ measured by the motion oscillator measuring unit 210 and the latest natural angular velocity $\omega_M=(\omega_{ML}, \omega_{MR})$ stored in the memory (s020 in FIG. 2). The first model is a model which expresses the correlation of a plurality of first elements, such as the left and right legs, whose outputs change in accordance with the first motion oscillator such as the hip joint angular velocity $d\phi_H/dt$. Specifically, the "first model" is a model for generating an output oscillation signal (that is, the output oscillation signal of each of the first elements) that changes over time at an angular velocity determined based on the natural angular velocity, by mutual entrainment with an input oscillation signal. The first model is expressed, for example, by the van der Pol equations represented by the following expressions (1). As the hip joint angular velocity $d\phi_H/dt$ (first motion oscillator) is input to the first model as the input oscillation signal by the first oscillator generating unit 220, the first oscillator $x=(x_L, x_R)$ is generated as the output oscillation signal.

$$(d^2x_L/dt^2) = \xi(1-x_L^2)(dx_L/dt) - \omega_{ML}^2 x_L + g(x_L - x_R) + K(d\phi_{HL}/dt),$$

$$(d^2x_R/dt^2) = \xi(1-x_R^2)(dx_R/dt) - \omega_{MR}^2 x_R + g(x_R - x_L) + K(d\phi_{HR}/dt) \quad (1)$$

where "$\zeta$" is a coefficient (>0) that is set so that the first oscillator x and its one-time temporal differentiation (dx/dt) draw stable limit cycles on the x–(dx/dt) plane. "g" is a first correlation factor representing the correlation of the left and right legs (first elements) in the first model. "K" is a feedback coefficient. It is noted that the natural angular velocity $\omega_M$ may be set arbitrarily within the range not largely deviating from the actual walking assist rhythm (walking induction rhythm) by the walking motion induction device 20.

The first oscillator $x=(x_L, x_R)$ is calculated or generated according to the Runge-Kutta method. The components $x_L$ and $x_R$ of the first oscillator x represent the walking assist rhythms for the left and right legs, respectively. The oscillator x tends to oscillate or periodically change at an autonomous rhythm or angular velocity reflecting the natural angular velocity $\omega_M$, while being harmonized with the hip joint angular velocity $d\phi_H/dt$ that changes over time at the rhythm or angular velocity approximately the same as that of the actual walking motion, by virtue of the "mutual entrainment" which is a property of the van der Pol equation.

It is noted that the first oscillator x may be generated based on any kind of oscillator that oscillates in a rhythm reflecting the user's walking motion rhythm (motion rhythm), such as a hip joint angle $\phi_H$, angle or angular velocity of knee joint, ankle joint, shoulder joint, elbow joint or the like, the walker's landing sound, respiratory sound, intermittently generated voice sound, or the like, instead of or in addition to the hip joint angular velocity $d\phi_H/dt$.

Further, the first model may be expressed by a van der Pol equation in the form different from that of the van der Pol equation represented by the expression (1). The first model may be expressed by any kind of equation that can generate an oscillator with the effect of mutual entrainment with the motion oscillator such as the hip joint angular velocity $d\phi_H/dt$.

As described above, the first oscillator x is generated as an output of the first element, according to the first model which represents the relationship of the plurality of first elements (left and right legs) whose outputs change in accordance with the motion oscillator such as the hip joint angular velocity $d\phi_H/dt$ (expression (1), s020 in FIG. 2). Accordingly, an appropriate first oscillator x can be generated in consideration of the relationship between the plurality of first elements, by allowing the correlation between the plurality of first elements concerning the user's actual motion to be reflected to the first correlation factor g and the like in the first model. For example, in the case where the left and right legs, or a plurality of joints of the same leg, are assumed as the plurality of first elements, the first oscillator x is generated so as to reflect the qualitative relationship between the left and right legs such as their alternate backward and forward movements, or the qualitative relationship between the joints of the same leg such as the period or phase difference between the leg motion around the hip joint and the leg motion around the knee joint. This allows the rhythm and scale of the induction oscillator inducing the user's motion to be set as appropriate in consideration of the relationship concerned.

Subsequently, the natural angular velocity setting unit 230 newly sets the natural angular velocity $\omega_M$ according to a virtual model including two virtual oscillators, based on the target phase difference $\delta\theta_d$ stored in the memory and the first oscillator x generated by the first oscillator generating unit 220 (s030 in FIG. 2).

Specifically, the first phase difference setting unit 231 firstly sets, for each of the left and right components, a phase difference $\theta_H - \theta_M$ between the phase $\theta_H$ of the hip joint angular velocity (first motion oscillator) $d\theta_H/dt$ measured by the motion oscillator measuring unit 210 and the phase $\theta_M$ of the first oscillator x generated by the first oscillator generating unit 220, as a first phase difference $\delta\theta_1$ (s031 in FIG. 2).

Next, on the condition that the first phase difference $\delta\theta_1$ set by the first phase difference setting unit 231 remained constant over the past three walking periods, the second phase difference setting unit 232 sets the phase difference $\theta_h - \theta_m$ between the virtual motion oscillator $\theta_h$ and the virtual induction oscillator $\theta_m$ represented by the following expression (2.3) as a second phase difference $\delta\theta_2$, for each of the left and right components, according to the "virtual model" represented by the following expressions (2.1) and (2.2) (s032 in FIG. 2).

$$d\theta_h/dt = \omega_h + \epsilon \cdot \sin(\theta_{mL} - \theta_{hL}) \quad (2.1)$$

$$d\theta_m/dt = \omega_m + \epsilon \cdot \sin(\theta_{hL} - \theta_{mL}) \quad (2.2)$$

$$\delta\theta_2 = \arcsin[(\omega_h - \omega_m)/2\epsilon] \quad (2.3)$$

where $\epsilon = (\epsilon_L, \epsilon_R)$ is a correlation factor between the virtual motion oscillator $\theta_h = (\theta_{hL}, \theta_{hR})$ and the virtual induction oscillator $\theta_m = (\theta_{mL}, \theta_{mR})$ in the virtual model for each of the left and right components. Further, $\omega_h$ is an angular velocity of the virtual motion oscillator $\theta_h$, and $\omega_m$ is an angular velocity of the virtual induction oscillator $\theta_m$.

Subsequently, the correlation factor setting unit 233 sets a correlation factor $\epsilon$ such that the difference $\delta\theta_1 - \delta\theta_2$ between the first phase difference $\delta\theta_1$ set by the first phase difference setting unit 231 and the second phase difference $\delta\theta_2$ set by the second phase difference setting unit 232 becomes minimal (s033 in FIG. 2).

Specifically, the correlation factor $\epsilon$ in a discrete time $t_{id}$ (d=1, 2, . . . ) where the hip joint angular velocity (motion oscillator) $d\phi_H/dt$ becomes 0 is sequentially set for each of the left and right components, according to the following expression (2.4).

$$\epsilon(t_{id+1}) = \epsilon(t_{id}) - \eta\{V_1(t_{id+1}) - V_1(t_{id})\}/\{\epsilon(t_{id}) - \epsilon(t_{id-1})\},$$

$$V_1(t_{id+1}) \equiv (1/2)\{\delta\theta_1(t_{id+1}) - \delta\theta_2(t_{id})\}^2 \quad (2.4)$$

where each component of $\eta = (\eta_L, \eta_R)$ is a coefficient which represents stability of the potential $V = (V_L, V_R)$ that causes each of the left and right components of the first phase difference $\delta\theta_1$ to approach the corresponding component of the second phase difference $\delta\theta_2$.

Next, on the condition that the angular velocity $\omega_m$ of the virtual induction oscillator $\theta_m$ is constant, the first angular velocity setting unit 234 sets the angular velocity $\theta_h$ of the virtual motion oscillator $\theta_h$ according to the following expression (2.5), for each of the left and right components, based on the correlation factor $\epsilon$ set by the correlation factor setting unit 233, so that each component of the difference $\delta\theta_1 - \delta\theta_2$ between the first and second phase differences becomes minimal (s034 in FIG. 2).

$$\omega_h(t_{id}) = -\alpha \int dt \left( [4\epsilon(t_{id})^2 - \{\omega_h(t) - \omega_m(t_{id})\}^2]^{1/2} \times \right.$$
$$\left. \sin[\sin^{-1}\{(\omega_h(t) - \omega_m(t_{id-1}))/2\epsilon(t_{id})\} - \delta\theta_1(t_{id})] \right) \quad (2.5)$$

where each component of $\alpha = (\alpha_L, \alpha_R)$ is a coefficient which represents stability of the system.

Subsequently, the second angular velocity setting unit 235 sets the angular velocity $\omega_m$ of the virtual induction oscillator $\omega_m$ as a new natural angular velocity $\omega_M$, for each of the left and right components, based on the angular velocity $\omega_h$ of the virtual motion oscillator $\theta_h$ set by the first angular velocity setting unit 234 (s035 in FIG. 2). Specifically, the second angular velocity setting unit 235 sets the angular velocity $\omega_m = (\omega_{mL}, \omega_{mR})$ of the virtual induction oscillator $\theta_m$ according to the following expression (2.6), for each of the left and right components, so that the second phase difference $\delta\theta_2$ approaches the target phase difference $\delta\theta_d$.

$$\omega_m(t_{id}) = \beta \int dt \cdot ([4\epsilon(t_{id})^2 - \{\omega_h(t_{id}) - \omega_m(t)\}^2 \times \sin[\sin^{-1}\{(\omega_h(t_{id}) - \omega_m(t))/2\epsilon(t_{id})\} - \delta\theta_d]) \quad (2.6)$$

where each component of $\beta = (\beta_L, \gamma_R)$ is a coefficient representing stability of the system.

Subsequently, the second oscillator generating unit 240 generates a second oscillator $y = (y_{L+}, y_{L-}, y_{R+}, y_{R-})$ according to a second model, based on the hip joint angle $\phi_H$ measured by the motion oscillator measuring unit 210 and the new natural angular velocity $\omega_M$ set by the natural angular velocity setting unit 230 (s040 in FIG. 2). The second model is a model which represents correlation between a plurality of second elements such as a plurality of neural elements whose outputs change in accordance with the motion oscillator such as the hip joint angle $\theta_H$. More specifically, the second model is expressed by the following simultaneous differential equations (3), which include: a motion variable $u_i$ (i=L+, L−, R+, R−) corresponding to changes in membrane potential of neural elements L+ and L− which govern the motions of the left thigh in the bending direction (forward) and the stretching direction (backward), respectively, and neural elements R+ and R− which govern the motions of the right thigh in the bending direction and the stretching direction, respectively; and a self-control factor $v_i$ reflecting an adaptive effect of the neural element i.

$$\tau_{1L+} \cdot du_{L+}/dt = -u_{L+} + w_{L+/L-}y_{L-} + w_{L+/R+}y_{R+} - \lambda L v_{L+} + f_1(\omega_{ML}) + f_2(\omega_{ML})K(\phi_L),$$

$$\tau_{1L-} \cdot du_{L-}/dt = -u_{L-} + w_{L-/L+}y_{L+} + w_{L-/R-}y_{R-} - \lambda L v_{L-} + f_1(\omega_{ML}) + f_2(\omega_{ML})K(\phi_L),$$

$$\tau_{1R+} \cdot du_{R+}/dt = -u_{R+} + w_{R+/L+}y_{L+} + w_{R+/R-}y_{R-} - \lambda_R v_{R+} + f_1(\omega_{MR}) + f_2(\omega_{MR})K(\phi_R),$$

$$\tau_{1R-} \cdot du_{R-}/dt = -u_{R-} + w_{R-/L-}y_{L-} + w_{R-/R+}y_{R+} - \lambda_R v_{R-} + f_1(\omega_{MR}) + f_2(\omega_{MR})K(\phi_R),$$

$$\tau_{2i} \cdot dv_i/dt = -v_i + y_i,$$

$$y_i = H(u_i - u_{th}), H \equiv 0(u_i < u_{th}), 1(u_i \geq u_{th}) \text{ or}$$

$$y_i = fs(u_i) \equiv 1/\{1 + \exp(-u_i/\xi)\} \quad (3)$$

where $\tau_{1i}$ is a time constant which defines change characteristics of the state variable $u_i$ and it has a dependence on the new natural angular velocity $\omega_M$ as expressed by the following expression (3.1) for each of the left and right components.

$$\tau_{1i} \equiv t(\omega_{ML})/\omega_{ML} - \gamma_L (i = L+, L-), t(\omega_{MR})/\omega_{MR} - \gamma_R (i = R+, R-) \quad (3.1)$$

where "$t(\omega)$" is a coefficient having a dependence on $\omega$. "$\gamma = (\gamma_L, \gamma_R)$" is a constant. "$\tau_{2i}$" is a time constant which defines change characteristics of the self-control factor $v_i$. "$w_{i/j}$ ($<0$)" is a second correlation factor representing the correlation between a plurality of second elements i and j. "$\lambda_L$" and "$\lambda_R$" are habituation coefficients. "K" is a feedback coefficient in accordance with the hip joint angle $\phi_H$.

"$f_1$" and "$f_2$" are functions defined by the following expressions (3.2) and (3.3), respectively.

$$f_1(\omega) \equiv c \cdot \omega \quad (c > 0) \quad (3.2)$$

$$f_2(\omega) \equiv c_0 + c_1 \omega + c_2 \omega^2 \quad (3.3)$$

The coefficients c, $c_0$, $c_1$, $c_2$ of $f_1(\omega_M)$ and $f_2(\omega_M)$, the functions of the new natural angular velocity $\omega_M$, may be set as coefficients corresponding to a target motion rhythm set by a target motion setting unit 211.

It is noted that the second oscillator $y_i$ may be generated based on any kind of oscillator that oscillates in a rhythm linked to the walking motion rhythm, such as a hip joint angular velocity $d\phi_H/dt$, angle or angular velocity of knee joint, ankle joint, shoulder joint, elbow join or the like, the walker's landing sound, respiratory sound, intermittently generated voice sound, or the like, instead of or in addition to the hip joint angle $\theta_H$.

The second oscillator $y_i$ is 0 when the value of the motion variable $u_i$ is less than a threshold value $u_{th}$; while when the value of the motion variable $u_i$ is not less than the threshold value $u_{th}$, it takes the value of $u_i$. Alternatively, the second oscillator $y_i$ is defined by a sigmoid function fs (see the expression (3)). Thus, for the motions of the thighs in the bending direction (forward), the second oscillators $y_{L+}$ and $y_{R+}$ corresponding to the outputs of the second elements (neural elements) L+ and R+, respectively, which govern those motions become greater than the outputs of the other second elements. Further, for the motions of the thighs in the stretching direction (backward), the second oscillators $y_{L-}$ and $y_{R-}$ corresponding to the outputs of the second elements L− and R−, respectively, which govern those motions become greater than the outputs of the other second elements. The frontward or backward motion of the leg (thigh) is identified, e.g., by the polarity of the hip joint angular velocity $d\phi_H/dt$.

As described above, the second oscillator $y_i$ is generated as the output of the second element i, according to the second model which expresses the relationship between a plurality of second elements whose outputs change according to the motion oscillator such as the hip joint angular velocity $d\phi_H/dt$ (the expression (3), s040 in FIG. 2). Thus, by causing the relationship between the plurality of second elements concerning the user's actual motion to be reflected to the second correlation factor $w_{i/j}$ in the second model, an appropriate second oscillator $y_i$ may be generated in consideration of the relationship between the actual elements. For example, in the case where the user's neurons are assumed to be the actual elements, the second oscillator $y_i$ is generated in the form reflecting the qualitative relationship between the neurons governing the walking by the left and right legs or the like. This enables the rhythm and scale of the induction oscillator inducing the user's motion to be set as appropriate in consideration of the relationship concerned.

Figure 3:
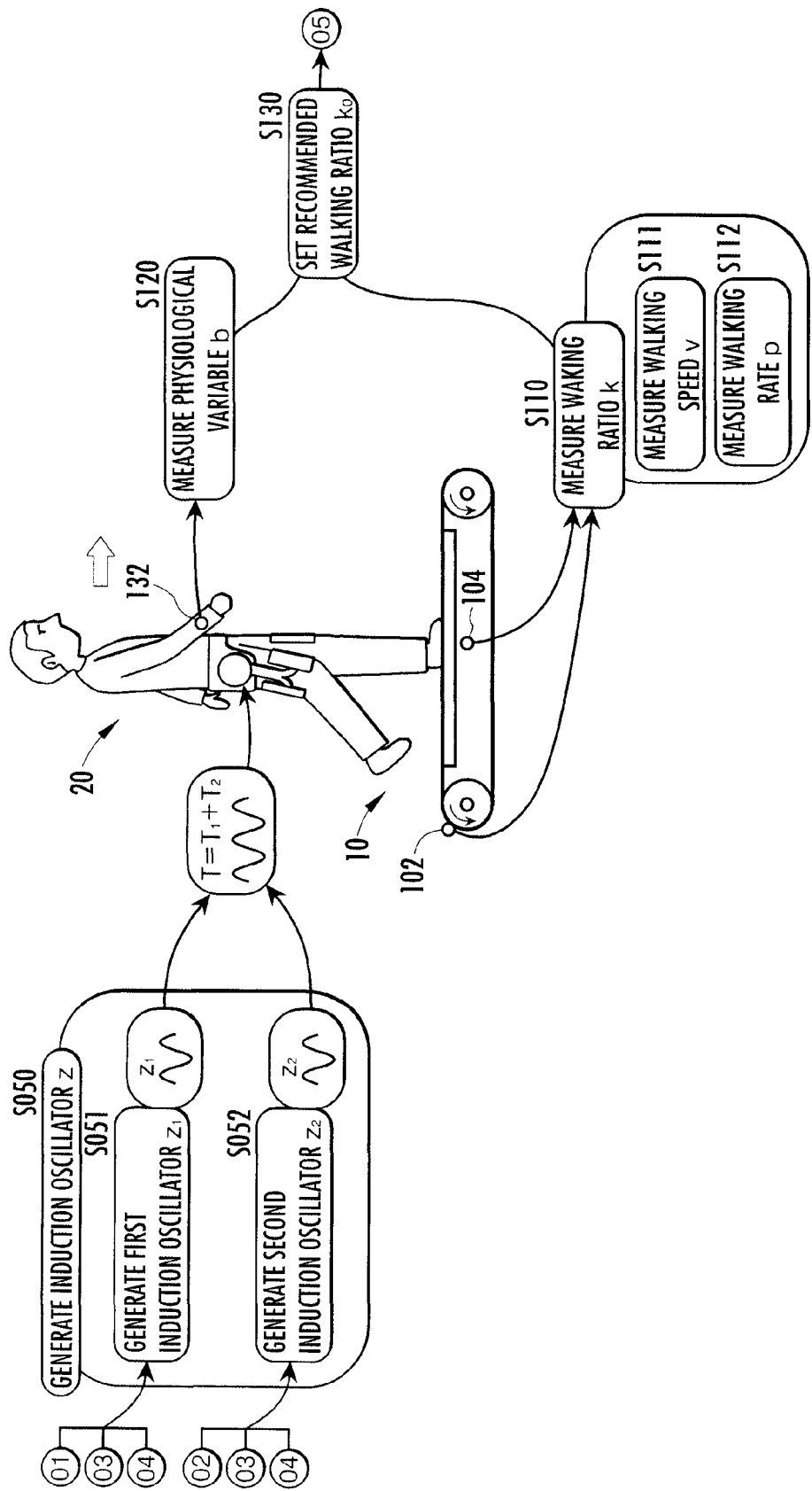
FIG. 3 is another explanatory diagram regarding the exercise management method of the present invention.

Next, the induction oscillator generating unit 250 generates the induction oscillator z, based on the hip joint angle (third motion oscillator) $\phi_H$ and the hip joint angular velocity (fourth motion oscillator) $d\phi_H/dt$ measured by the motion oscillator measuring unit 210, the second oscillator $y_i$ generated by the second oscillator generating unit 240, and the new natural angular velocity $\omega_M$ set by the natural angular velocity setting unit 230 (s050 in FIG. 3).

Specifically, a first induction oscillator $z_1$ is generated according to the following expression (4) (s051 in FIG. 3).

$$z_{1L} = g_{1+}(\omega_{mL})g_+(\phi_{HL})y_{L+} - g_{1-}(\omega_{mL})g_-(\phi_{HL})y_{L-},$$

$$z_{1R} = g_{1+}(\omega_{mR})g_+(\phi_{HR})y_{R+} - g_{1-}(\omega_{mR})g_-(\phi_{HR})y_{R-} \quad (4)$$

where "$g_{1+}$", "$g_{1-}$", "$g_+$", and "$g_-$" are functions defined by the following expressions (4.1) to (4.4), respectively.

$$g_{1+}(p, \omega) \equiv \Sigma_k a_{k+} \omega^k \ (a_{k+}: \text{coefficient}, k=0 \text{ to } 3) \quad (4.1)$$

$$g_{1-}(p, \omega) \equiv \Sigma_k a_{k-} \omega^k \ (a_{k-}: \text{coefficient}, k=0 \text{ to } 3) \quad (4.2)$$

$$g_+(\phi) \equiv c_{1+}(\phi - \phi_{0+}) + c_{2+}(\phi - \phi_{0+})^3 \ (c_{1+}, c_{2+}: \text{coefficients}; \phi_{0+}: \text{target value of hip joint angle } \phi_H \text{ in bending direction}) \quad (4.3)$$

$$g_-(\phi) \equiv c_{1-}(\phi - \phi_{0-}) + c_{2-}(\phi - \phi_{0-})^3 \ (c_{1-}, c_{2-}: \text{coefficients}; \phi_{0-}: \text{target value of hip joint angle } \phi_H \text{ in stretching direction}) \quad (4.4)$$

Figure 4:
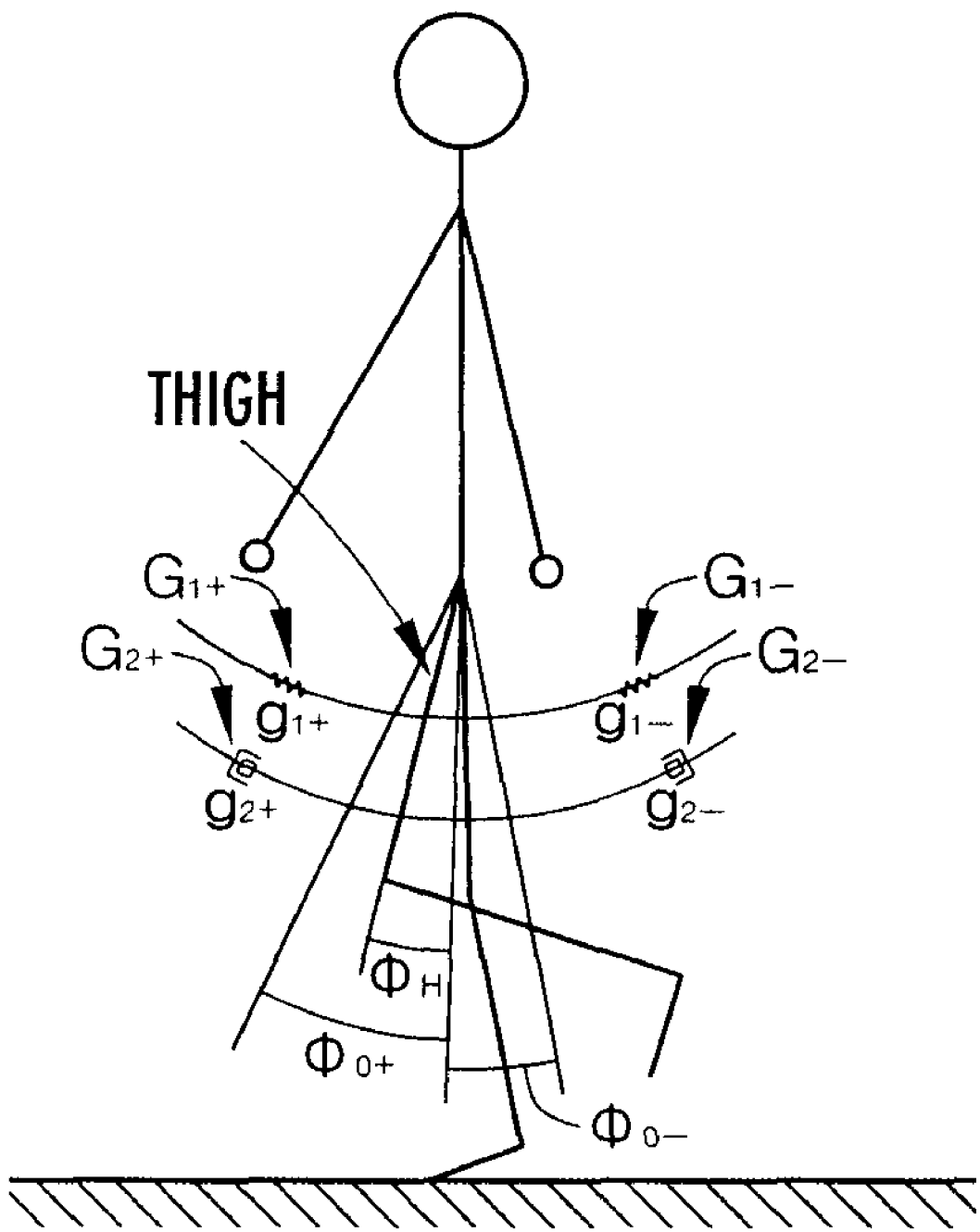
FIG. 4 is an explanatory diagram of virtual springs and dampers inducing walking motion.

The first induction oscillator $z_1$ represents elastic forces of two virtual springs $G_{1+}$ and $G_{1-}$, as shown in FIG. 4, which have the first coefficients $g_{1+}$ and $g_{1-}$, respectively, as their spring coefficients (elastic coefficients). The first coefficients $g_{1+}$ and $g_{1-}$ represent the gradients of a first potential (a potential of a virtual elastic element) which cause the hip joint angle (third motion oscillator as the motion variable in accordance with the user's motion scale) $\phi_H$ to approach the target angles $\phi_{0+}$ ($>0$) and $\phi_{0-}$ ($<0$) in accordance with the target motion scale, according to the natural angular velocity $\omega_M$ (see the expressions (4.1) and (4.2)). That is, the first induction oscillator $z_1$ represents elastic forces of the elastic elements such as the virtual springs which have the first coefficients $g_{1+}$, $g_{1-}$ as the elastic coefficients (spring coefficients) and which restore the value of the hip joint angle (third motion oscillator) $\phi_H$ to the target angles $\phi_{0+}$ and $\phi_{0-}$. This enables the user's motion to be induced with the rhythm and scale reflecting the elastic elements of the user's body such as the elastic force generated during the transition from the muscle contraction state to the muscle stretch state.

The elastic force of the virtual spring $G_{1+}$ represents the force that acts on the user's thigh to bring the hip joint angle $\theta_H$ close to its target value $\phi_{0+}$ according to the spring coefficient $g_{1+}$ (see the expression (4)). Specifically, when the hip joint angle $\theta_H$ is less than the target angle $\theta_{0+}$, the elastic force of the spring $G_{1+}$ represents the force that acts on the thigh in such a way as to move the thigh in the direction of increasing the hip joint angle $\theta_H$ (forward). When the hip joint angle $\theta_H$ exceeds the target angle $\theta_{0+}$, the elastic force of the spring $G_{1+}$ represents the force that acts on the thigh in such a way as to move the thigh in the direction of decreasing the hip joint angle $\theta_H$ (backward).

Moreover, the elastic force of the other virtual spring $G_{1-}$ represents the force that acts on the user's thigh to bring the hip joint angle $\theta_H$ close to the target angle $\theta_{0-}$ according to the spring coefficient $g_{1-}$ (see the expression (4)). Specifically, when the hip joint angle $\theta_H$ exceeds the target angle $\phi_{0-}$, the elastic force of the spring $G_{1-}$ represents the force that acts on the thigh in such a way as to move the thigh in the direction of decreasing the hip joint angle $\theta_H$ (backward). When the hip joint angle $\theta_H$ is less than the target angle $\theta_{0-}$, the elastic force of the spring $G_{1-}$ represents the force that acts on the thigh in such a way as to move the thigh in the direction of increasing the hip joint angle $\theta_H$ (forward).

Further, as described above, there are uneven outputs from some of the plurality of second elements i (=L+, L−, R+, R−) in accordance with the forward or backward movement of the thighs, which prevents the elastic forces of the two virtual springs $G_{1+}$ and $G_{1-}$ from being cancelled out.

Specifically, in the case where the left thigh is moving forward, the value of the second oscillator $y_{L+}$ corresponding to the output of the second element L+, which is one of the elements governing this motion, becomes greater than the value of the second oscillator $y_{L-}$ corresponding to the output of the second element L−, which is the other element governing this motion. Accordingly, the first induction oscillator $z_{1L}$ represented by the expression (4) is approximated by the following expression (4a).

$$z_{1L} \approx g_{1+}(\omega_{mL})g_{+}(\phi_{HL})y_{L+} \qquad (4a)$$

Therefore, in the case where the left thigh is moving forward, of the elastic forces of the two virtual springs $G_{1+}$ and $G_{1-}$, the elastic force of the spring $G_{1+}$ acting on the user's thigh in such a way as to bring the hip joint angle $\theta_H$ close to the target angle $\phi_{0+}$ for the front side is reflected predominantly. This avoids cancellation of the elastic forces of the two virtual springs $G_{1+}$ and $G_{1-}$ with each other.

Further, in the case where the left thigh is moving backward, the output of the second element L−, which is one of the elements governing this motion, or, the value of the second oscillator $y_{L-}$, becomes greater than the output of the other second element L+, or, the value of the second oscillator $y_{L+}$. Accordingly, the first induction oscillator $z_{1L}$ represented by the expression (4) is approximated by the following expression (4b).

$$z_{1L} \approx g_{1-}(\omega_{mL})g_{-}(\phi_{HL})y_{L-} \qquad (4b)$$

Therefore, in the case where the left thigh is moving backward, of the elastic forces of the two virtual springs $G_{1+}$ and $G_{1-}$, the elastic force of the spring $G_{1-}$ acting on the user's thigh in such a way as to bring the hip joint angle $\phi_H$ close to the target angle $\phi_{0-}$ for the back side is reflected predominantly. This avoids cancellation of the elastic forces of the two virtual springs $G_{1+}$ and $G_{1-}$ with each other. The same applies to the motion of the right leg (thigh).

It is noted that a sigmoid function fs (see the expression (3)) having the hip joint angular velocity $d\phi_H/dt$ as a variable may be incorporated into the first coefficients $g_{1+}$, $g_{1-}$, and a first torque $T_1$ may be generated in the form unevenly reflecting part of the second oscillators $y_i$ as the outputs of the plurality of second elements i, in accordance with the forward or backward movement of the thigh specified by the polarity of the hip joint angular velocity $d\phi_H/dt$. This again prevents the elastic forces of the two virtual springs $G_{1+}$ and $G_{1-}$ from being cancelled out.

Furthermore, a second induction oscillator $z_2$ is set according to the following expression (5) (s052 in FIG. 2).

$$z_{2L} = -g_{2+}(\omega_{mL})(d\phi_{HL}/dt)H_{+}(\phi_{HL})y_{L+} + \qquad (5)$$
$$g_{2-}(\omega_{mL})(d\phi_{HL}/dt)H_{-}(\phi_{HL})y_{L-},$$
$$z_{2R} = -g_{2+}(\omega_{mR})(d\phi_{HR}/dt)H_{+}(\phi_{HR})y_{R+} +$$
$$g_{2-}(\omega_{mR})(d\phi_{HR}/dt)H_{-}(\phi_{HR})y_{R-}$$

where "$g_{2+}$", "$g_{2-}$", "$H_{+}$", and "$H_{-}$" are functions defined by the following expressions (5.1) to (5.4), respectively.

$$g_{2+}(\omega) = \Sigma_k b_{k+}\omega^k \; (b_{k+}\text{: coefficient, k=0 to 3}) \qquad (5.1)$$

$$g_{2-}(\omega) = \Sigma_k b_{k-}\omega^k \; (b_{k-}\text{: coefficient, k=0 to 3}) \qquad (5.2)$$

$$H_{+}(\phi) = 0(\phi \leq 0), 1(\phi > 0) \qquad (5.3)$$

$$H_{-}(\phi) = 0(\phi > 0), 1(\phi \leq 0) \qquad (5.4)$$

The second induction oscillator $z_2$ is understood as damping forces of two virtual dampers $G_{2+}$ and $G_{2-}$, as shown in FIG. 4, which have the second coefficients $g_{2+}$ and $g_{2-}$, respectively, as damper coefficients (damping coefficients). The second coefficients $g_{2+}$ and $g_{2-}$ represent the gradients of a second potential (a potential of a virtual damper (damping element)) which suppress an increase in absolute value of the hip joint angle $\theta_H$ according to the natural angular velocity $\omega_M$ (see the expressions (5.1) and (5.2)). That is, the second induction oscillator $z_2$ is represented as damping forces of the damping elements such as the virtual dampers which have the second coefficients $g_{2+}$, $g_{2-}$ as the damping coefficients (damper coefficients) and which suppress an increase in absolute value of the hip joint angle (third motion oscillator) $\phi_H$ according to the hip joint angular velocity (fourth motion oscillator) $d\phi_H/dt$. This enables the user's motion to be induced with the rhythm and scale reflecting the damping elements of the user's body such as the viscous force generated during the transition from the muscle stretch state to the muscle flexed state.

The damping force of one virtual damper $G_{2+}$, represents the force that acts on the user's thigh to prevent an increase in absolute value of the hip joint angle $\theta_H$ toward the front side (bending side), according to the damper coefficient $g_{2+}$, and the hip joint angular velocity $d\phi_H/dt$ (see the expression (5)). In other words, the damping force of the virtual damper $G_{2+}$ represents the force that acts on the thigh in such a way as to prevent the excessive forward movement of the thigh.

Moreover, the elastic force of the other virtual damper $G_{2-}$ represents the force that acts on the user's thigh to prevent an increase in absolute value of the hip joint angle $\theta_H$ toward the back side (stretch side), according to the damper coefficient $g_{2-}$ and the hip joint angular velocity $d\phi_H/dt$ (see the expression (5)). In other words, the damping force of the virtual damper $G_{2-}$ represents the force that acts on the thigh in such a way as to prevent the excessive backward movement of the thigh.

Furthermore, the second induction oscillator $z_2$ includes step functions $H_+$ and $H_-$ as the functions of the hip joint angle $\theta_H$. This prevents the damping forces of the two virtual dampers $G_{2+}$ and $G_{2-}$ from being cancelled out.

Then, the currents $I(z)=(I_L(z_{1L}+z_{2L}), I_R(z_{1R}+z_{2R})$ corresponding to the induction oscillator $z$ ($=z_1+z_2$) including the first induction oscillator $z_1=(z_{1L}, z_{1R})$ and the second induction oscillator $z_2=(z_{2L}, z_{2R})$ generated by the induction oscillator generating unit 250 are supplied from the battery 206 to the left and right actuators 210, respectively, thereby causing the forces (torques around the hip joints) $T(I)$ corresponding to the supplied currents I to act on the user's thighs.

Thereafter, the above-described processing (s011, s012, ..., s040 in FIG. 2 and s050 in FIG. 3) is repeated to allow the user to walk, with the torque T around the hip joint applied to the user by the operation of the walking motion induction device 20.

Then, with the user's walking motion induced by the operations of the treadmill 10 and the walking motion induction device 20 as described above, the motion variable measuring unit 110 measures the walking ratio k (s110 in FIG. 3). Specifically, the first motion variable measuring unit 111 measures the user's walking speed v based on the output of the speed sensor (first sensor) 102 responsive to the speed of the belt 13 of the treadmill 10 (s111 in FIG. 3). Further, the second motion variable measuring unit 112 measures the user's walking rate (the number of steps per unit time) p based on the number of times that the output of the pressure sensor (second sensor) 104 responsive to the pressure applied to the footplate 14 of the treadmill 10 attains the peak per unit time (s112 in FIG. 3). The walking rate p may be measured based on the change over time of the torque T around the hip joint applied to the user by the walking motion induction device 20. Further, an acceleration sensor may be attached to the user's body, and the walking rate p may be measured based on the output of the acceleration sensor responsive to the acceleration in the vertical direction of the user. Then, the motion variable measuring unit 110 measures the walking ratio $k=v/p^2$ which is a function of the walking speed v and the walking rate p.

The physiological variable measuring unit 120 measures a physiological variable b based on an output of the physiological variable sensor 106 (s120 in FIG. 3). The physiological variable b may include a part or all of the user's oxygen uptake, respiratory frequency, heart rate, pulse rate, blood pressure, arterial oxygen saturation, lactate level, myogenic potential, and consumed energy.

Every time the physiological variable b is measured, part or all of the target angles $\phi_{0+}$ and $\phi_{0-}$ of the hip joint angle $\theta_H$, the coefficients $a_{k+}$ and $a_{k-}$ included in the respective first coefficients $g_{1+}(\omega_M)$ and $g_{1-}(\omega_M)$, and the coefficients $b_{k+}$ and $b_{k-}$ included in the respective second coefficients $g_{2+}(\omega_M)$ and $g_{2-}(\omega_M)$ are updated. Updating the target angles $\phi_{0+}$ and $\phi_{0-}$ may change the induction scale by the walking motion induction device 20, resulting in modification of the user's step width q. Further, updating a part or all of the coefficients $a_{k+}$, $a_{k-}$, $b_{k+}$, and $b_{k-}$ may change the induction rhythm by the walking motion induction device 20, resulting in modification of the user's walking rate (target motion rhythm) p. In this manner, the physiological variable b is measured sequentially in the state where the user's walking motion is induced with the walking ratio k changed sequentially by the walking motion induction device 20. Then, the relationship between the walking ratio k and the physiological variable b is obtained, and the recommended walking ratio setting unit 130 sets a recommended walking ratio $k_0$ based on the relationship concerned (s130 in FIG. 3).

Figure 5:
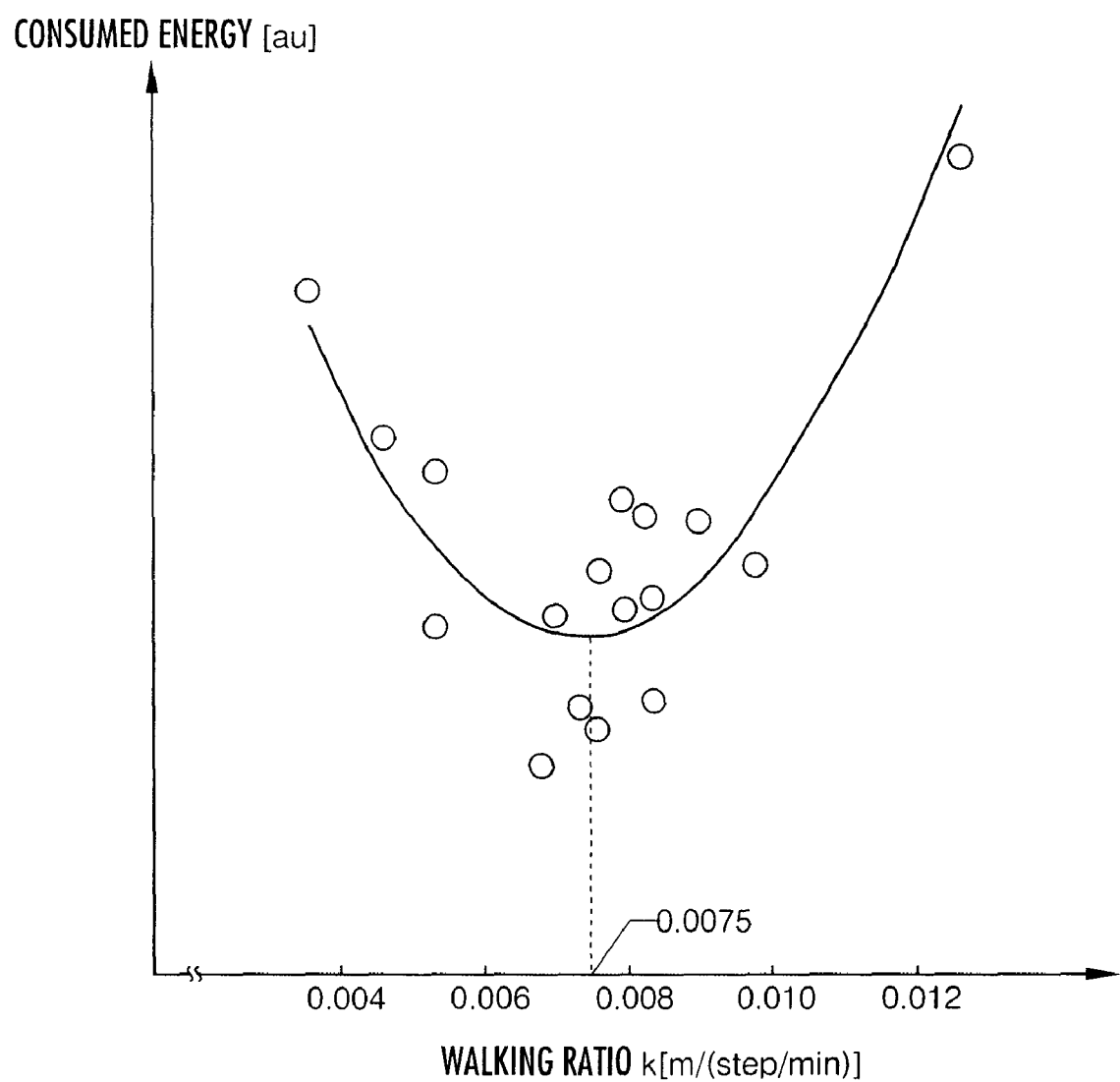
FIG. 5 is an explanatory diagram regarding a method for setting a recommended walking ratio.

For example, assume that the energy consumed by the user is measured as the physiological variable b and that the relationship between the walking ratio k and the consumed energy (physiological variable) as indicated by the circles (O) in FIG. 5 is obtained. In this case, the relationship concerned is approximated by the quadric curve of the walking ratio k shown in FIG. 5, and the walking ratio k=0.0075 corresponding to the minimal value of the quadric curve is set as the recommended walking ratio $k_0$ for the user. The recommended walking ratio $k_0$, which is set to minimize the user's consumed energy, is an appropriate walking ratio k in consideration of reduction of the body load of the user. It is noted that the physiological variable b other than the consumed energy, such as the heart rate, lactate level (representing the degree of fatigue of the user's body), muscle group activity (representing the degree of activation of the physical functions) or the like, may be measured, and the recommended walking ratio $k_0$ may be set based on the measured variable b.

Now, a method of inducing the user's walking motion by the walking motion induction device 20 according to the recommended walking ratio $k_0$ will be described with reference to FIG. 6. The method of inducing the user's walking motion in accordance with the recommended walking ratio $k_0$ differs from the method of inducing the user's walking motion at the time of setting the recommended walking ratio $k_0$ only in the method of generating the induction oscillator z (s050 in FIG. 3). Therefore, description will not be repeated for measurement of the motion oscillator (s011 and s012 in FIG. 2), generation of the first oscillator x (s020 in FIG. 2), setting of the natural angular velocity $\omega_M$ (s030 in FIG. 2), and generation of the second oscillator y (s040 in FIG. 2).

Figure 6:
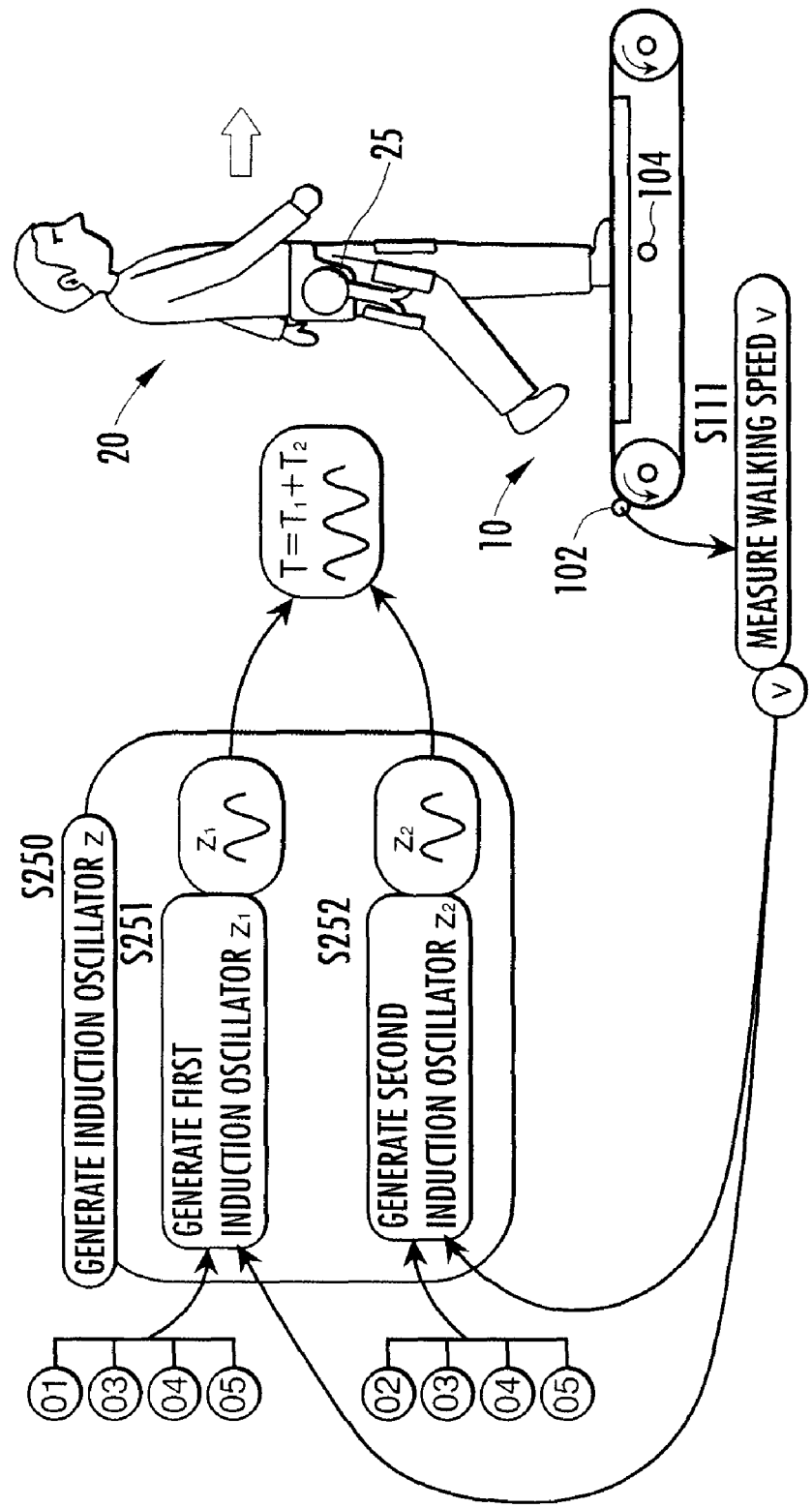
FIG. 6 is another explanatory diagram regarding the exercise management method of the present invention.

The first motion variable measuring unit 111 measures the walking speed v of the user whose walking motion is induced by the operation of the treadmill 10 and the operation of the walking motion induction device 20 (s111 in FIG. 6).

Further, the induction oscillator generating unit 250 generates the induction oscillator z, based on the hip joint angle $\phi_H$ and the hip joint angular velocity $d\phi_H/dt$ measured by the motion oscillator measuring unit 210, the second oscillator $y_i$ generated by the second oscillator generating unit 240, and the natural angular velocity $\omega_M$ set by the natural angular velocity setting unit 230, and also based on the user's walking speed v measured by the first motion variable measuring unit 111 and the recommended walking ratio $k_0$ set by the recommended walking ratio setting unit 130 (s250 in FIG. 6).

Specifically, a first induction oscillator $z_1$ is generated according to the following expression (6) (s251 in FIG. 6).

$$z_{1L} = g_{1+}(p_0, \omega_{mL})g_+(q_0, \phi_{HL})y_{L+} - g_{1-}(p_0, \omega_{mL})g_-(q_0, \phi_{HL})y_{L-}, \quad (6)$$

$$z_{1R} = g_{1+}(p_0, \omega_{mR})g_+(q_0, \phi_{HR})y_{R+} - g_{1-}(p_0, \omega_{mR})g_-(q_0, \phi_{HR})y_{RR-},$$

$$p_0 \equiv (v/k_0)^{1/2}, \quad q_0 \equiv (vk_0)^{1/2}$$

where "$g_{1+}$", "$g_{1-}$", "$g_+$", and "$g_-$" are functions defined by the following expressions (6.1) to (6.4), respectively.

$$g_{1+}(p_0,\omega) \equiv \Sigma_k a_{k+}(p_0)\omega^k \quad (a_{k+}(p_0): \text{coefficient, } k=0 \text{ to } 3) \quad (6.1)$$

$$g_{1-}(p_0,\omega) \equiv \Sigma_k a_{k-}(p_0)\omega^k \quad (a_{k-}(p_0): \text{coefficient, } k=0 \text{ to } 3) \quad (6.2)$$

$$g_+(q_0,\phi) \equiv c_{1+}(\phi-\phi_{0+}(q_0))+c_{2+}(\phi-\phi_{0+}(q_0))^3 \quad (c_{1+}, c_{2+}: \text{coefficients}; \phi_{0+}: \text{target value of hip joint angle } \phi_H \text{ in bending direction}) \quad (6.3)$$

$$g_-(q_0,\phi) \equiv c_{1-}(\phi-\phi_{0-}(q_0))+c_{2-}(\phi-\phi_{0-}(q_0))^3 \quad (c_{1-}, c_{2-}: \text{coefficients}; \phi_{0-}: \text{target value of hip joint angle } \phi_H \text{ in stretching direction}) \quad (6.4)$$

The first induction oscillator $z_1$ allows the user's walking motion to be induced so that the hip joint angle (third motion oscillator) $\phi_H$ matches the target angle $\phi_{0+}$, $\phi_{0-}$ corresponding to the recommended walking ratio $k_0$ and the walking speed v.

Furthermore, a second induction oscillator $z_2$ is generated according to the following expression (7) (s252 in FIG. 6).

$$z_{2L} = -g_{2+}(p_0, \omega_{mL})(d\phi_{HL}/dt)H_+(\phi_{HL})y_{L+} + \tag{7}$$
$$g_{2-}(p_0, \omega_{mL})(d\phi_{HL}/dt)H_-(\phi_{HL})y_{L-},$$
$$z_{2R} = -g_{2+}(p_0, \omega_{mR})(d\phi_{HR}/dt)H_+(\phi_{HR})y_{R+} +$$
$$g_{2-}(p_0, \omega_{mR})(d\phi_{HR}/dt)H_-(\phi_{HR})y_{R-}$$

where "$g_{2+}$" and "$g_{2-}$" are functions defined by the following expressions (7.1) and (7.2), respectively.

$$g_{2+}(p_0,\omega) = \Sigma_k b_{k+}(p_0)\omega^k (b_{k+}(p_0): \text{coefficient}, k=0 \text{ to } 3) \tag{5.1}$$

$$g_{2-}(p_0,\omega) = \Sigma_k b_{k-}(p_0)\omega^k (b_{k-}(p_0): \text{coefficient}, k=0 \text{ to } 3) \tag{5.2}$$

The second induction oscillator $z_2$ allows the user's walking motion to be induced so as to suppress an increase in absolute value of the hip joint angle $\theta_H$ according to the hip joint angular velocity $d\phi_H/dt$.

The target angles $\phi_{0-}(q_0)$ and $\phi_{0-}(q_0)$ of the hip joint angle $\theta_H$ are each a function of a recommended step width $q_0$ $(=(vk_0)^{1/2})$ corresponding to the recommended walking ratio $k_0$ and the walking speed v, and may be corrected based on the deviation $\delta q$ of the user's step width q $(=v/p)$ from the recommended step width $q_0$.

Further, the coefficients $a_{k+}(p_0)$ and $a_{k-}(p_0)$ included in the first coefficients $g_{1+}(p_0, \omega_M)$ and $g_{1-}(p_0, \omega_M)$ and the coefficients $b_{k+}(p_0)$ and $b_{k-}(p_0)$ included in the second coefficients $g_{2+}(p_0, \omega_M)$ and $g_{2-}(p_0, \omega_M)$ are each a function of the recommended walking rate $p_0$ $(=(v/k_0)^{1/2})$ corresponding to the recommended walking ratio $k_0$ and the walking speed v, and may be corrected based on the deviation $\delta p$ of the user's walking rate p $(=v/q)$ from the recommended walking rate $p_0$.

Then, the current I corresponding to the induction oscillator z including the first induction oscillator $z_1$ and the second induction oscillator $z_2$ generated by the induction oscillator generating unit 250 is supplied from the battery 206 to the left and right actuators 210 to cause the forces (torques around the hip joints) T to be acted on the user's thighs.

Thereafter, the above-described processing (s011, s012, ..., s040 in FIG. 2, s250 in FIG. 6) is repeated to allow the user to walk in the state where the torque T around the hip joint is applied by the operation of the walking motion induction device 20.

According to the exercise management system 1 exerting the above-described functions, the walking ratio (motion variable) k and the physiological variable b are measured in the state where the user's motion is induced by the operation of the walking motion induction device (second motion induction device) 20 (s110, s120 in FIG. 3). Then, the value of the walking ratio k at the time when the physiological variable b attains an appropriate value in consideration of "activation of the physical functions" or "reduction of the body load" of the animal is set as a recommended walking ratio $k_0$. This ensures that the recommended walking ratio $k_0$ is set as appropriate in consideration of activation of the user's physical functions or the like. The user's walking motion is induced by the walking motion induction device 20 in accordance with the recommended walking ratio $k_0$, which allows the induction scale and rhythm to be controlled appropriately so that the user's step width (motion scale) q and the walking rate (motion rhythm) p become appropriate in consideration of activation of the physical functions of the user or the like.

Results of experiments regarding the effects of the exercise management system 1 will now be described with reference to FIGS. 7 to 9.

Figure 7:
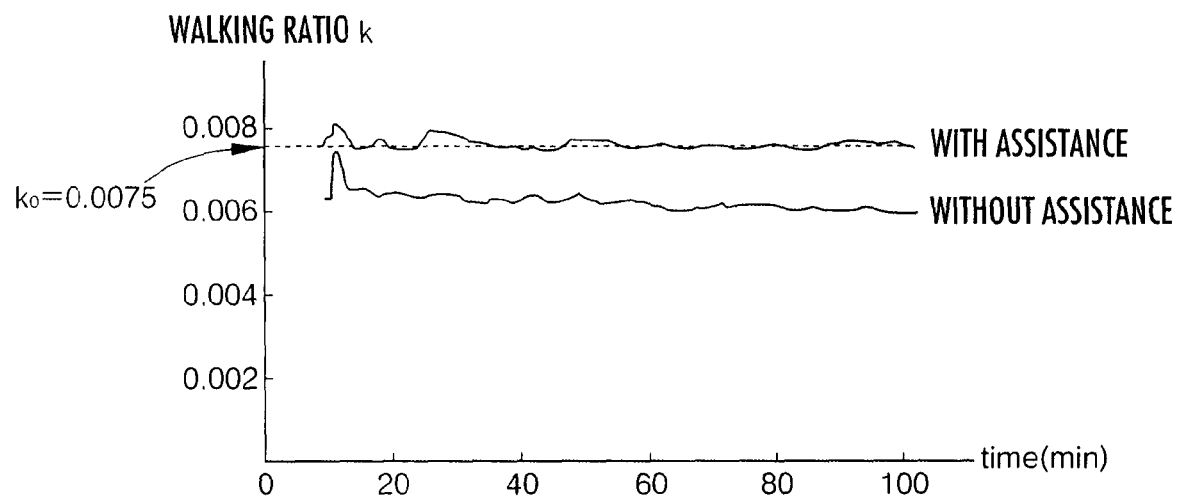
FIG. 7 is an explanatory diagram showing experimental results regarding the effects of the exercise management system of the present invention.

As shown in FIG. 7, even if the same user walks at the same speed v, the walking ratio k varies according to whether the walking motion of the user is induced by the walking motion induction device 20. Specifically, when the user walks without wearing the walking motion induction device 20, the walking ratio k is controlled to about 0.0065. By comparison, in the case where the user walks wearing the walking motion induction device 20 that induces the walking motion, the walking ratio $k_0$ is controlled to a recommended walking ratio k (=0.0075) that has been set as described above. The walking motion of this user is induced by the operation of the walking motion induction device 20 so that the walking ratio k and, hence, the step width q increases.

Figure 8:
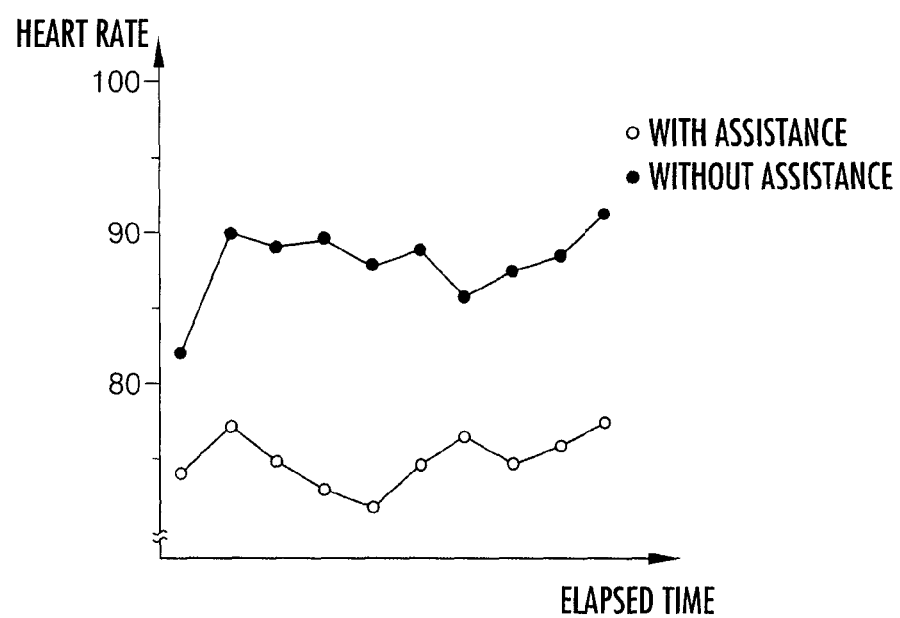
FIG. 8 is another explanatory diagram showing experimental results regarding the effects of the exercise management system of the present invention.

Further, as shown in FIG. 8, the heart rate (physiological variable) of the same user walking at the same speed v varies depending on presence/absence of guidance of the walking motion by the walking motion induction device 20. Specifically, the heart rate when the user is walking without wearing the walking motion induction device 20 is higher than the heart rate when the user is walking wearing the walking motion induction device 20 that induces the walking motion. This means that the heart rate is restricted low and the load on the body is reduced in the state where the walking motion is induced to increase the user's step width as shown in FIG. 7.

Figure 9A:
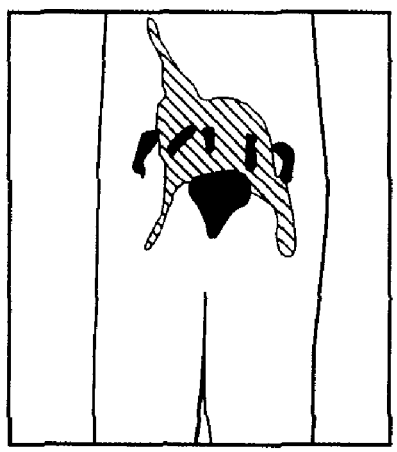
FIG. 9 is another explanatory diagram showing experimental results regarding the effects of the exercise management system of the present invention.
Figure 9B:
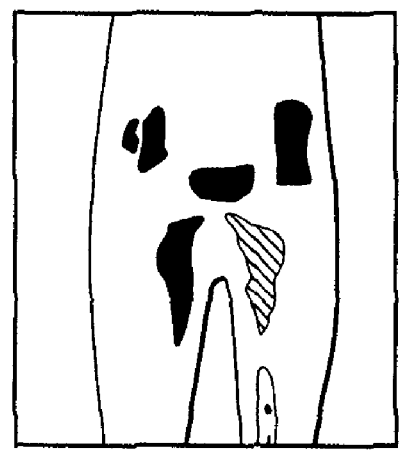

Furthermore, as shown in FIG. 9, the muscle group activity (physiological variable) in the case where the same user walks at the same speed v varies according to whether the walking motion is induced by the walking motion induction device 20. The muscle group activity around the hip joints in the case where the user is walking wearing the walking motion induction device 20 and the walking motion is induced thereby, as shown in FIG. 9(b), is higher than the muscle group activity of the same sites when the user is walking without wearing the walking motion induction device 20, as shown in FIG. 9(a). This means that the user's physical functions are activated as the user's walking motion is induced to increase the step width as shown in FIG. 7.

The results of the experiments shown in FIGS. 7 to 9 indicate the important meaning of using the exercise management system 1 for managing exercise of, e.g., the user with motor deterioration like an aged person. In other words, the use of the exercise management system 1 of the present invention suppresses degradation of, and promotes activation of, the physical functions, while reducing the body load of the aged person or the like.

Further, the user's walking speed (first motion variable) v is measured based on the speed of the belt 13 of the treadmill 10 (s111 in FIG. 3). Furthermore, the user's walking rate (second motion variable) p is measured based on the pressure applied to the treadmill 10 which varies with repeated landing on and leaving from the floor of the user (s112 in FIG. 3). This improves the measurement accuracy of the walking ratio k which is a function of the walking speed v and the walking rate p (s110 in FIG. 3). Accordingly, it is possible to more accurately set the recommended value of the motion variable as appropriate in consideration of activation of the physical functions and/or reduction of the body load of the user.

The circular movement of the endless belt (circular motion body) 13 of the treadmill 10 induces walking or running motion in the direction opposite from the movement of the endless belt 13. This enables the movement of the user by the walking or running to be cancelled out by the circular movement of the endless belt 13, thereby allowing setting of the recommended walking ratio $k_O$ for the user's walking or running motion only if there is a space for installing the treadmill 10. The recommended walking ratio $k_O$ may be set in the state where the user's walking motion is induced by the walking motion induction device 20 alone, without intervention of the treadmill 10.

It is noted that the exercise management system 1 may be used for setting a recommended value of the motion variable that varies with any motion other than the user's walking motion. For example, in the case where the hands are used to apply forces to the left and right wheels of a wheelchair, it may be used for setting a recommended value of a motion variable for another motion, such as the rhythm of pushing the wheels with the arms. The exercise management system 1 may also be used for setting a recommended value of a motion variable for motion of an animal other than the human being, such as running motion of a horse or the like. Furthermore, instead of the walking ratio k, a recommended value of a motion variable as an arbitrary function of the walking speed v and the walking rate p may be set.

Moreover, for the first motion induction device, a device other than the treadmill 10 may be adopted, which induces the motion of the user's physical site, such as the leg or arm, that comes into contact with a circular motion body, by circular movement of the circular motion body. The circular motion body may be: an endless belt looped over a plurality of rollers; a spherical body or oval sphere circulated about an axis passing the center or a point offset from the center; a tubular body such as a cylinder or square pole circulated about a central axis or an axis offset from and parallel to the central axis; or a block of substance circulated about an arbitrary axis.

In the above-described embodiment, the torques $T=(T_L, T_R)$ around the left and right hip joints in accordance with the induction oscillator z are applied to the user's body. Alternatively, the torques around various joints, such as knee joint, ankle joint, shoulder joint, elbow joint and carpal joint, may be applied to the user's body. The combination of the joints to which the torques are to be applied may be changed for each user.

Further, in the case where the magnitude of periodical change of the hip joint angle $\theta_H$ or the hip joint angular velocity $d\phi_H/dt$ (motion oscillator) measured by the motion oscillator measuring unit 210 exceeds a threshold value, the second oscillator generating unit 240 of the second control unit 200 may generate the second oscillator y that oscillates in the rhythm or angular velocity determined based on one or both of the angular velocity (change of the phase over time) such as the hip joint angle $\theta_H$ measured by the motion oscillator measuring unit 210 and the angular velocity of the first oscillator x generated by the first oscillator generating unit 220, instead of the new natural angular velocity $\omega_M$ set by the natural angular velocity setting unit 230.

According to this configuration, even if the user's motion rhythm changes abruptly, the user's motion can be induced with an appropriate rhythm corresponding to the changed motion rhythm.

The induction oscillator z may be generated according to the method as disclosed in Japanese Patent Application Laid-Open No. 2004-73649.

Furthermore, the induction oscillator z may be generated in the following manner.

The motion oscillator measuring unit 210 measures motion oscillators which are parameters changing over time in accordance with the user's different body parts (for example, a shoulder joint angular velocity and a hip joint angle) as a "first motion oscillator" and a "second motion oscillator", respectively. The first oscillator generating unit 220 generates a first oscillator x which attains mutual entrainment with the first motion oscillator and which changes over time at an angular velocity determined based on a natural angular velocity $\omega_M$. Further, the natural angular velocity setting unit 230 sets a new natural angular velocity $\omega_M$ based on the phase difference between the first motion oscillator and the first oscillator x. The second oscillator generating unit 240 generates a second oscillator y which changes over time at an angular velocity determined based on the new natural angular velocity $\omega_M$, based on the second motion oscillator. Then, the induction oscillator generating unit 250 generates an induction oscillator z based on one or both of the walking speed v (first motion variable) measured by the first motion variable measuring unit 111 and the walking rate p (second motion variable) measured by the second motion variable measuring 112, in addition to the second oscillator y.

According to this configuration, the user's motion can be induced so that the user's motion rhythm approaches the target motion rhythm, while harmonizing the motion rhythms of the user's different body parts with the rhythm of inducing the motion.

Further, in the exercise management system 1 of the present invention, the recommended walking ratio setting unit 130 may preliminarily set a plurality of recommended walking ratios $k_O$ for a plurality of users, respectively, by recognizing a plurality of identifiers for identification of the physical characteristics (including the body size, weight, age, gender and the like) of the respective users, and set a new recommended walking ratio $k_O$ based on the recommended walking ratio $k_O$ preliminarily set for each identifier recognized, to thereby establish a database having the identifiers and the recommended values associated with each other. In this case, the user's walking motion is induced based on the typical recommended value retrieved from the database in accordance with the user's identifier and hence the physical characteristics. This allows the induction scale and rhythm to be controlled appropriately so that the user's walking ratio k becomes appropriate in consideration of activation of the user's physical functions or the like.

The invention claimed is:

1. An exercise management system for managing exercise of an animal, comprising:

a first motion induction device which is operative to induce motion of the animal by applying a force to the animal;

a second motion induction device including a first orthosis and a second orthosis attached to the animal, an actuator mounted to the first orthosis, and a force transmitting member connected to the actuator and the second orthosis, the second motion induction device being operative to induce motion of the animal while adjusting a motion scale of the animal by applying a force to the animal at a rhythm harmonized with a motion rhythm of the animal, with the actuator applying a force to the animal via the force transmitting member and the second orthosis;

a control unit which controls an operation of the second motion induction device;

a first motion variable measuring unit which measures a first motion variable representing a speed of the motion of the animal that is moving while being induced by an operation of the first motion induction device, based on an output signal of a first sensor provided in the first motion induction device, the first sensor outputting a signal responsive to a speed of the operation of the first motion induction device;

a second motion variable measuring unit which measures a second motion variable representing a motion rhythm of the animal, based on either a pattern of change over time of an output signal of a second sensor provided in the first motion induction device or an operating state of the second motion induction device controlled by the control unit, the second sensor outputting a signal responsive to a force of interaction between the first motion induction device and the animal;

a motion variable measuring unit which measures a value of a function having the first motion variable and the second motion variable as variables, as a value of the motion variable, based on a measurement value of the first motion variable measured by the first motion variable measuring unit and a measurement value of the second motion variable measured by the second motion variable measuring unit;

a physiological variable measuring unit which measures a physiological variable based on an output signal of a physiological variable sensor, the physiological variable sensor outputting a signal responsive to a physiological condition of the animal; and a recommended value setting unit which sets, as a recommended value of the motion variable, the motion variable that is measured by the motion variable measuring unit at the time when the physiological variable measured by the physiological variable measuring unit during a process where the animal is moving while being induced by the operation of the second motion induction device that is controlled by the control unit to change the motion variable attains an appropriate value in consideration of activation of physical functions or reduction of body load of the animal.

2. The exercise management system according to claim 1, wherein the first motion variable measuring unit measures a walking or running speed of the animal as the first motion variable, and the second motion variable measuring unit measures a step width of the animal or a walking rate corresponding to the number of steps per unit time of the animal as the second motion variable.

3. The exercise management system according to claim 2, wherein the motion variable measuring unit measures, as the motion variable, a walking ratio corresponding to either a ratio of a square of the step width as the second motion variable with respect to the walking or running speed as the first motion variable, or a ratio of the walking or running speed as the first motion variable with respect to a square of the walking rate as the second motion variable.

4. The exercise management system according to claim 1, wherein the first motion variable measuring unit measures the first motion variable of the animal based on a speed of rotation of a rotating body provided in the first motion induction device, the motion of the animal being induced in a direction opposite from the direction in which a body part of the animal that is in contact with the rotating body receives a force from the rotating body with rotation of the rotating body.

5. The exercise management system according to claim 1, wherein the first motion variable measuring unit measures a walking or running speed as the first motion variable which represents a speed of walking or running motion of the animal that is induced in a direction opposite from the movement of an endless belt serving as a rotating body that is looped over a plurality of rollers provided in a treadmill serving as the first motion induction device, based on a driven speed of the endless belt.

6. The exercise management system according to claim 1, wherein the recommended value setting unit preliminarily sets a plurality of said recommended values for a plurality of animals, respectively, by recognizing identifiers for identification of physical characteristics of the respective animals, and sets a new recommended value based on the recommended value preliminarily set for each identifier recognized, to establish a database having the identifiers and the recommended values associated with each other.

* * * * *